United States Patent [19]

Easmunt et al.

[11] Patent Number: 4,981,572
[45] Date of Patent: Jan. 1, 1991

[54] ELECTRODE UNIT AND PACKAGE FOR A BLOOD ANALYZER

[75] Inventors: Henry C. Easmunt, Millville; Benito Sopranzetti, Jr., Lawrenceville, both of N.J.

[73] Assignee: Glastron, Inc., Mount Laurel, N.J.

[21] Appl. No.: 207,636

[22] Filed: Jun. 16, 1988

[51] Int. Cl.$^5$ .................. G01N 27/36; G01N 27/333
[52] U.S. Cl. ....................... 204/420; 204/153.15; 204/408; 204/409; 204/416; 204/435
[58] Field of Search ............... 204/408, 409, 416, 418, 204/419, 420, 435, 153.15

[56] References Cited

U.S. PATENT DOCUMENTS

| | | | |
|---|---|---|---|
| 3,244,607 | 4/1966 | Leonard et al. | 204/405 |
| 3,556,950 | 1/1971 | Dahms | 204/435 |
| 3,700,577 | 10/1972 | Graver | 204/420 |
| 3,840,438 | 10/1974 | Ast et al. | |
| 3,853,732 | 12/1974 | Brand et al. | |
| 4,206,027 | 6/1980 | Schindler et al. | 204/412 |
| 4,321,544 | 3/1982 | Riseman | |
| 4,379,029 | 4/1983 | Yeager | 204/415 |
| 4,551,222 | 11/1985 | Uematsu et al. | 204/435 |
| 4,565,665 | 1/1986 | Pogt | 204/435 |
| 4,600,494 | 7/1986 | Bromberg et al. | |
| 4,647,362 | 3/1987 | Watanabe | 204/416 |
| 4,661,236 | 4/1987 | Gelo et al. | |
| 4,687,500 | 8/1987 | Gelo et al. | |
| 4,711,703 | 12/1987 | Wright et al. | 204/408 |
| 4,758,325 | 7/1988 | Kanno et al. | 204/418 |
| 4,791,932 | 12/1988 | Margules | 204/409 |

Primary Examiner—T. Tung
Attorney, Agent, or Firm—John F. A. Earley; John F. A. Earley, III; P. Michael Walker

[57] ABSTRACT

An electrode unit for use in an analyzer of blood and of liquids includes a cylindrical outer housing having open ends and a pair of top hat end plate bushings each having a central bore and a plug portion, the bushings being positioned in each end of the housing with the plug portion directed into the housing to form a filling chamber with the inner surface of the housing. A sodium glass capillary tube is mounted in the bores of the bushings. An annular groove is formed in an end flange portion of each bushing so that a connecting alignment ring may seat in the bushing annular grooves of two adjacent electrode units to center the electrode units.

8 Claims, 3 Drawing Sheets

ELECTRODE UNIT AND PACKAGE FOR A BLOOD ANALYZER

BACKGROUND OF THE INVENTION

1. Field Of The Invention

This invention relates to blood and liquid analyzers, and more particularly concerns an electrode unit and an electrode package for use in an analyzer of blood and of liquids.

2. Description Of The Prior Art

Prior art blood analyzers have included a package of electrode units arranged in series and in abutting relationship so that a single blood sample may be passed through a series of electrode units to determine the contents in the blood of selected components such as potassium, sodium, and carbon dioxide. Such conventional electrode units have run into problems which have produced inaccurate readings For example, the readings from a sodium electrode may drift because of changes in ambient temperature, because of electrical noise, and because of carry over from one blood sample to the next, even though there is a wash-out cycle between blood samples.

Passing the blood sample from one electrode unit to the next has been a problem which conventional electrode unit packages have tried to solve by providing washer seals of Teflon synthetic fluorine-containing resin between electrode units. But the Teflon synthetic fluorine-containing resin flows and creates obstructions to the passage of the blood which causes turbulence and electrical noise which throws off the reading.

Also, conventional electrode units contain a bottle with an upper neck and two side arm port passages The interior elements of the electrode unit including the bottle are encapsulated in an insulating material The process of encapsulating the interior elements often cracked the bottle which is weak, and the bottle would break at the shoulder portion of the side arms during the encapsulating, or the bottle would break when force was exerted on a package of abutting electrode units to hold them together in alignment. If insufficient force is exerted on the ends of the electrode unit package, the elements of the electrode unit did not hold their alignment. If too much force is exerted on the ends of the electrode unit package to hold them together in alignment, the bottle breaks, and the filler solution in the bottle leaks out For further background in this art, U.S. Patent No. 3,853,732, issued Dec. 10, 1974, to Brand and Rao, is incorporated herein by reference.

SUMMARY OF THE INVENTION

It is an object of this invention to provide an electrode unit for use in liquid analyzers of blood and other liquids which overcomes the problems of the prior art, and which holds the elements of the electrode unit in proper alignment, and which does not break when force is applied to a series of electrode units to hold them in alignment.

It is another object to provide a package which holds a series of electrode units in alignment in close abutting relationship so as to prevent the blood or other liquid from leaking between units It is believed that turbulence of the blood sample caused by misalignment of the elements of the electrode unit causes electrical noise which causes the electrical output to drift and produce inaccurate readings. It is an object of this invention to eliminate this electrical drift by eliminating misalignment and the resulting turbulence which it causes and thereby eliminate, or reduce, the drift caused by that turbulence It is another object of the invention to eliminate drift and inaccuracies caused by variation in ambient temperature. In one embodiment of the invention, this is accomplished by providing a sterilized cotton filler inside the ion exchange chamber of the electrode unit in order to change, or inhibit thermodynamic flow in and around the ion exchange chamber In another embodiment of the invention for reducing the variations in readings caused by changes in ambient temperature, a double housing is provided for impeding the flow of heat or cold from the ion exchange chamber In this manner the blood sample tube and the chamber through which it flows is protected from variations in ambient temperature surrounding the electrode unit.

DETAILED DESCRIPTION

Figure 4:
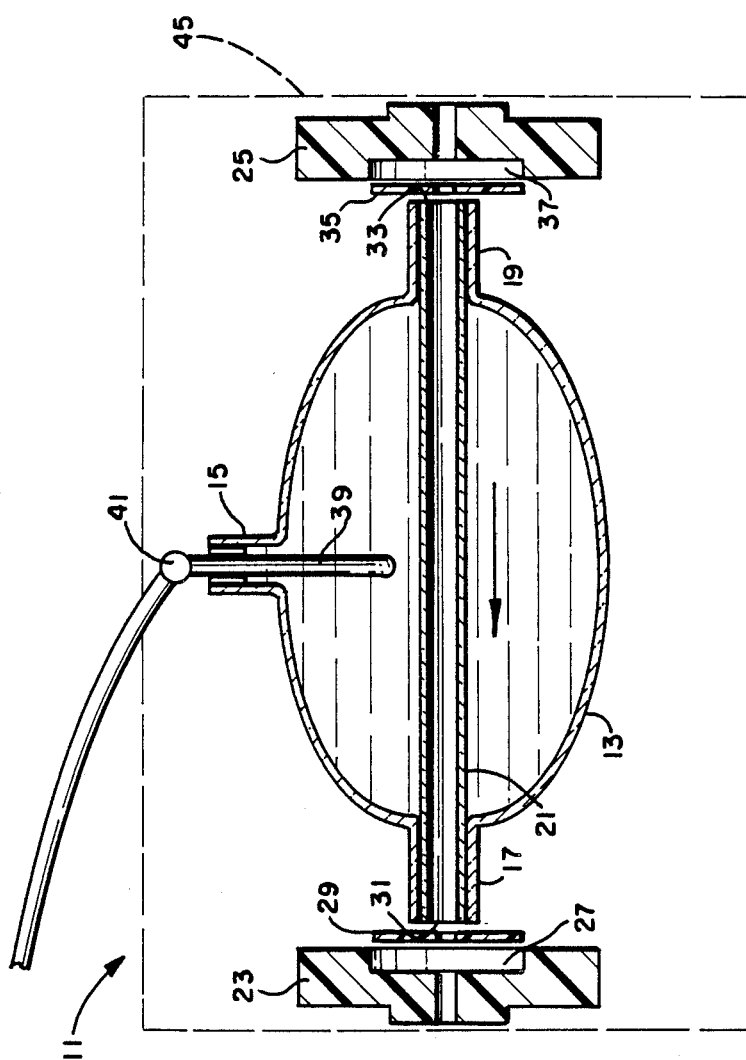
FIG. 4 shows a view in vertical section, and partly exploded, of a conventional electrode unit which includes a bottle with a neck and two side arms, and bushings, and Teflon washer seals. Teflon is a trademark of E.I. duPont de Nemours and Company, Wilmington, Delaware, for its synthetic flourine-containing resin.

Turning now to FIG. 4 of the drawings, there is shown a conventional electrode unit 11 for analyzing the sodium content of a blood sample, which comprises a bottle 13 made of Pyrex (a trademark of Corning Glass Works, Corning, N. Y. for its glassware) glass and provided with a neck 15 and two side arms 17 and 19. The bottle 13 is filled with a filler solution, such as a sodium chloride solution, and a sodium glass tube 21 is positioned in side arm 17, 19 and extends through the bottle in contact with the filler solution.

The side arms 17, 19 of the bottle 13 are supported by KEL F (a Trademark of E.I. duPont de Nemours and Company, Wilmington, Del., for its tri-fluoro-chloro-ethylene) bushings 23, 25.

Bushing 23 is provided with a recess 27, and a Teflon washer seal 29 seats in recess 27 and abuts against end 31 of sodium tube 21.

At the other end 33 of sodium tube 21, a similar Teflon washer seal 35 seats in a recess 37 in the end bushing 25, and washer seal 35 abuts against end 33 of tube 21.

A silver-silver chloride electrode 39 is mounted in the neck 15 of bottle 13 and extends downwardly into the bottle where it is surrounded by the filler solution.

A solder connection 41 attaches the upper end of electrode 39 to a coaxial cable which is attached to other elements of the blood analyzer. The electrode unit is encapsulated in a block 45 of insulating material.

Figure 1:
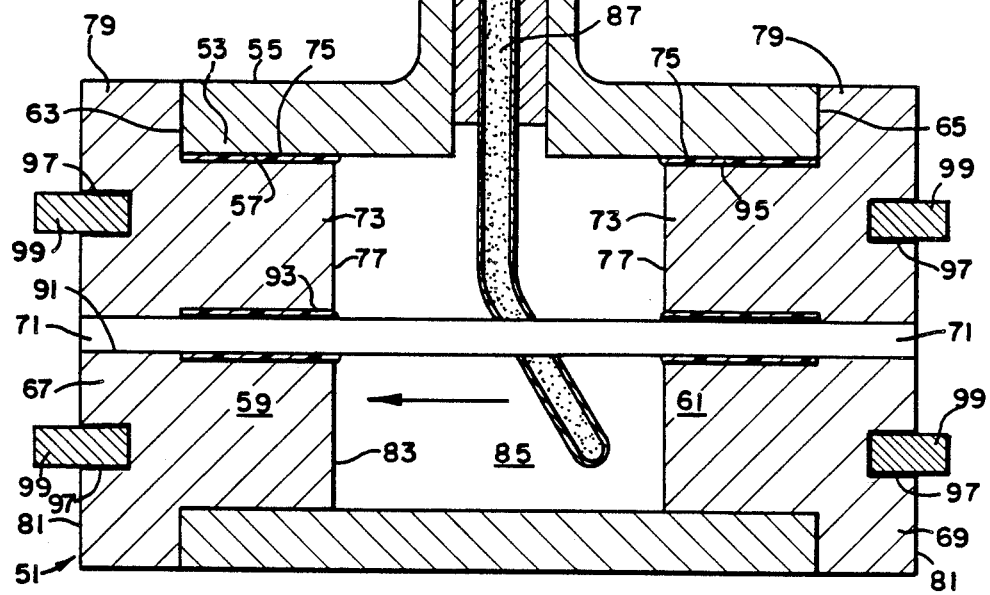
FIG. 1 is a view in vertical section of an electrode unit, for use with a blood or liquid analyzer, constructed in accordance with this invention.

Turning now to the inventive electrode unit for an analyzer machine for blood or other liquid, there is shown in FIG. 1 an electrode unit 51 which comprises a cylindrical outer housing 53, made of glass or acrylic material, having an outer surface 55, an inner surface 57 and open ends 59, 61 with end edges 63 and 65.

A pair of top hat end bushings 67, 69 each have a central bore 71 and a plug portion 73 with a cylindrical surface 75 and an inner end face 77. End bushings 67, 69 are also provided with an end flange portion 79 with an outer end face 81.

Bushing 67 is positioned in end 59 of housing 53 with plug portion 73 extending inside housing 53, and the flange portion 79 abutting against the end edges 63 of the outer housing 53.

Bushing 69 is positioned at end 61 of housing 53 with the plug portion 73 extending inside the housing 53 and the flange 79 abutting against the end edges 65 of outer housing 53.

The inner end faces 77 of bushings 67, 69 form a filling chamber 83 with the inner surface 57 of housing 53.

An ion conducting filling solution 85 is inside chamber 83, and a silver-silver halide electrode, such as silver-silver chloride electrode 87 is mounted in neck 89 of housing 53 and extends into the solution 85 in chamber 83.

A sodium glass capillary tube 91 is mounted in the bore 71 of bushings 67, 69 concentric with the outer housing 53 and extends between the ends of the bushings 67, 69 through the solution 85 in chamber 83.

An adhesive layer 93 seals the sodium tube 91 to the bushings 67, 69 and an adhesive layer 95 seals the bushings 67, 69 to the housing 53.

An annular groove 97 is formed in the outer end faces 81 of end bushings 67, 69, and a connecting alignment ring 99 is adapted to seat in the bushing annular grooves 97 of two adjacent electrode units 51 to center and align the electrode units. The height of the connecting alignment ring 99 is smaller than the depth of the two annular grooves 97, i.e., the combined depth, of the bushings 67, 69 of the connected bushings so that the outer faces 81 of the bushing flanges 79 may be pressed against each other to form a tight connection and avoid leakage of the blood or other liquid passing between adjacent electrode units.

An insulation material such as cotton (not shown in FIG. 1) may also be placed inside chamber 83, together with the ion conducting filling solution 85, to impede the flow of heat or cold from chamber 83 so as to diminish error caused by variations in ambient temperature and variations in filler solution temperature.

Figure 3:
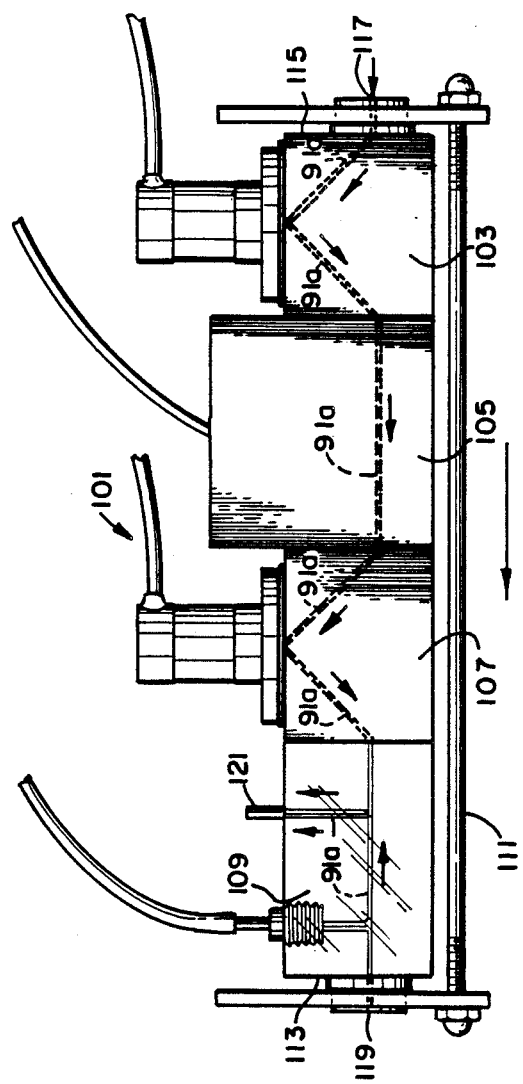
FIG. 3 shows a package of three electrode units and a reference unit held together in a close, abutting relationship.

Referring to FIG. 3, there is shown a package 101 of a series of electrodes, including a potassium electrode 103, a sodium electrode 105 constructed in accordance with this invention, a carbon dioxide electrode 107, and a reference electrode 109. Compressing means 111 are provided for exerting opposing longitudinal pressure on the ends 113, 115 of the package 101 of electrode units 103, 105, 107 and 109, to hold them tightly together in horizontal alignment, reduce turbulence and electrical noise caused by misalignment, and produce a more accurate reading. The blood or other liquid sample enters tubes or passageways 91a at entrance port 117 and passes through the electrodes 103, 105, 107 and into reference electrode 109 where it meets the reference solution which enters the tube or passageways 91a from entrance port 119. Both the blood sample and the reference solution exit from reference electrode 109 through exit port 121.

A package of electrode units that includes a conventional sodium electrode, such as electrode 11 in FIG. 4, cannot be tightened enough to prevent leakage of fluid between adjacent electrode units because the sodium electrode bottle 13 breaks before the seal is tight. Consequently, the package of electrode units requires Teflon washer seals positioned between adjacent electrode units to prevent liquid from leaking between the units, but the Teflon washer seals are not always effective in preventing leaks. The Teflon washer seals referred to here are in addition to Teflon washer seals 29, 35 referred to in FIG. 4.

The use of the inventive sodium electrode unit 105 in package 101 of FIG. 3 allows package 101 to be tightened by compressing means 111 so that fluid does not leak between adjacent units 103, 105, 107 and 109, and thus eliminates the need for Teflon washer seals between adjacent units.

Eliminating the need for Teflon washer seals from between adjacent electrode units of a package is advantageous because it prevents fluid leakage at the junction of adjacent electrode units, it prevents the collection of debris at the unction of adjacent electrode units, it removes a component of possible misalignment of adjacent electrode units and it prevents the problem of "cold flow" of the Teflon washer seals. "Cold flow" is the extrusion of Teflon material under pressure.

Figure 2:
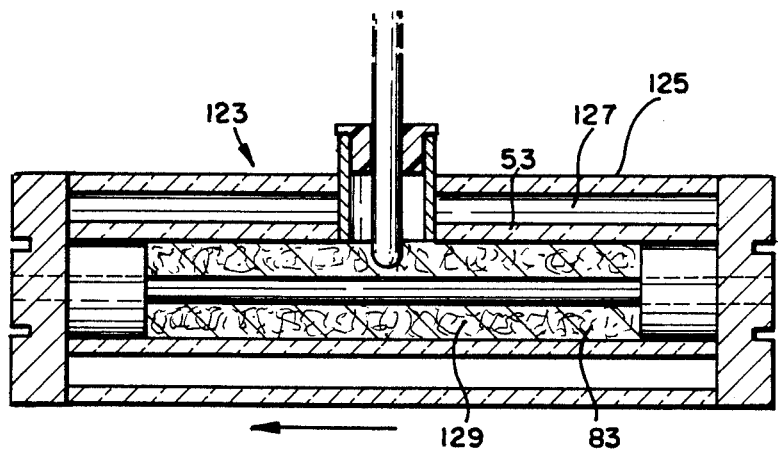
FIG. 2 is a view in vertical section of an alternative embodiment of the invention showing two housings and a cotton filler in the chamber of the electrode unit.

FIG. 2 discloses an alternative embodiment of the invention, an electrode unit 123 which is the same as electrode unit 51 except that it is provided with another outer glass shell 125 with a space 127 between shell 125 and housing 53 to impede the flow of heat or cold to or from chamber 83, and thus reduce the error caused by fluctuations in ambient temperature.

Also, cotton 129, or similar material is placed inside chamber 83 to impede the flow of heat or cold from chamber 83 so as to diminish error caused by variations in ambient temperature.

We claim:

1. An electrode unit for use in a package of a liquid analyzer machine for analyzing blood or other liquids and the like, comprising
   a cylindrical outer housing having outer and inner surfaces and open ends with end edges,
   a pair of top hat end bushings each having a central bore and having a plug portion, with a cylindrical surface and an inner end face, and an end flange portion with an outer end face,
   one of said bushings being positioned in each end of the outer housing with the plug portion of the bushing extending inside the housing and the flange of the bushing abutting against end edges of the outer housing, with the plug inner end faces forming a filling chamber with the inner surface of the housing,
   said bushing outer end faces being flat to fit flush against the flat outer end faces of the bushings of adjacent units,
   a filling solution inside the chamber,
   a silver-silver chloride electrode mounted on and extending through the outer housing into the solution in the chamber,
   a sodium glass capillary tube mounted in the bores of the bushings concentric with the outer housing and extending between the bushings through the solution in the chamber to the outer end faces of the bushings, adhesive means sealing the sodium tube to the bushings and sealing the bushings to the outer housing, said tube being adapted to contain a liquid sample to be analyzed, an annular groove formed in the flat outer end face of each bushing flange, an alignment ring for seating in the bushing annular grooves of two adjacent electrode units to center the electrode units, and the height of the alignment ring being smaller than the combined depths of two annular grooves of the bushings so that the outer faces of adjacent bushing flanges may be pressed against each other to form a tight connection and avoid leakage of the liquid sample passing between adjacent electrode units.

2. A package of two or more electrode units adapted to be mounted in side-by-side relationship in a liquid analyzer machine for analyzing blood or other liquids, at least one of said units comprising a cylindrical outer housing having outer and inner surfaces and open ends with end edges, a pair of bushings each having a central bore, one of said bushings mounted in each end of the housing and forming a chamber with the housing, said bushings having flat outer end faces fitting flush against the outer end faces of the bushings of adjacent units, a filling solution inside the chamber, an electrode mounted on the housing and extending into the chamber, a tube mounted in the bores of the bushings and extending through the chamber to the outer end faces of the bushings, an annular alignment groove formed in the outer end faces of each bushing, an alignment ring seated in the bushing annular grooves of two adjacent electrode units to center the electrode units, and compressing means exerting opposing longitudinal pressure on the ends of a package of two or more electrode units to hold them tightly together in horizontal alignment without sealing rings between adjacent units to reduce turbulence and electrical noise, and produce a more accurate reading of the amount of selected ingredient in the blood or other liquid.

3. A packaage of two or more electrode units adapted to be mounted in side-by-side relationship in a liquid analyzer machine for analyzing blood or other liquids, one of said units comprising a cylindrical outer housing having outer and inner surfaces and open ends with end edges, a pair of top hat end bushings each having a central bore and having a plug portion, with a cylindrical surface and an inner end face, and an end flange portion with an outer end face, one of said bushings being positioned in each end of the outer housing with the plug portion of the bushing extending inside the housing and the flange of the bushing abutting against end edges of the outer housing, with the plug end inner faces forming a filling chamber with the inner surface of the housing, said bushing outer end faces fitting flush against the outer end faces of the bushings of adjacent units, a filling solution inside the chamber, a silver-silver chloride electrode mounted on and extending through the outer housing into the solution in the chamber, a sodium glass capillary tube mounted in the bores of the bushings concentric with the outer housing and extending between the bushings through the solution in the chamber to the outer end faces of the bushing, adhesive means sealing the sodium tube to the bushings and sealing the bushings to the outer housing said tube being adapted to contain a liquid sample to be analyzed, an annular groove formed in the outer end face of each bushing flange, an alignment ring seated in the bushing annular grooves of two adjacent electrode units to center the electrode units, the height of the alignment ring being smaller than the combined depths two annular grooves of the bushings so that the electrode units may be pressed against each other to form a tight connection and avoid leakage of the liquid sample passing between adjacent electrode units, and compressing means exerting opposing longitudinal pressure on the ends of a package of two or more electrode units to hold them tightly together in horizontal alignment without sealing rings between adjacent ends to reduce turbulence and electrical noise, and produce a more accurate reading of the amount of selected ingredient in the blood or other liquid.

4. An electrode unit for use in a package of electrode units in a liquid analyzer machine for analyzing blood or other liquids, comprising a cylindrical outer housing having outer and inner surfaces and open ends with end edges, a pair of bushings each having a central bore, one of said bushings mounted in each end of the housing and forming a chamber with the housing, said bushings having flat outer end faces for fitting flush against outer end faces of the bushings of adjacent electrode units, a filling solution inside the chamber, a tube mounted in the bores of the bushings and extending through the chamber to a position flush with the outer end faces of the bushings, electrode means mounted on the housing, an annular alignment groove formed in the outer end face of each bushing, and an alignment ring for seating in the bushing annular grooves of two adjacent electrode units to center the electrode units.

5. The electrode unit of claim 4, including an outer shell outside the outer housing with a space between the shell and the housing to inhibit flow of heat or cold from the chamber due to variations in ambient temperature.

6. The electrode unit of claim 4, including insulation material positioned in the chamber to inhibit flow of heat or cold from the chamber due to variations in ambient temperature, and variations in fluid throughput temperature.

7. The electrode unit of claim 4, said tube being a sodium selective tube and said electrode unit being a sodium detecting electrode unit.

8. A package comprising two or more electrode units for use in a liquid analyzer machine for analyzing samples of blood or other liquids at least one unit comprising
- a cylindrical outer housing having outer and inner surfaces and open ends with end edges,
- a pair of bushings each having a central bore,
- one of said bushings mounted in each end of the housing,
- said bushings having flat outer end faces fitting flush against outer end faces of the bushings of adjacent units,
- a tube mounted in the bores of the bushings and extending through the electrode unit to the outer end faces of the bushings,
- electrode means mounted on the housing,
- an annular alignment groove formed in the outer end face of each bushing, and
- an alignment ring seated in the bushing annular grooves of two adjacent electrode units to center the electrode units, and compressing means exerting opposing longitudinal pressure on the ends of the package of two or more electrode units to hold them tightly together in horizontal alignment without sealing rings between adjacent units to reduce turbulence and electrical noise, and produce a more accurate reading of the amount of selected ingredients in the blood or other liquid.

* * * * *